(12) United States Patent
Pape (10) Patent No.: US 12,239,190 B2
(45) Date of Patent: Mar. 4, 2025

(54) OPTICAL FOOT SOLE SCANNING APPARATUS AND INSOLE PRODUCTION APPARATUS HAVING SAME, METHOD FOR ASCERTAINING A THREE-DIMENSIONAL SHAPE OF AN INSOLE AND METHOD FOR AUTOMATICALLY PRODUCING AN INSOLE (71) Applicant: Oliver Pape, Rastede (DE)

(72) Inventor: Oliver Pape, Rastede (DE)

( * ) Notice: Subject to any disclaimer, the term of this patent is extended or adjusted under 35 U.S.C. 154(b) by 354 days.

(21) Appl. No.: 17/766,169

(22) PCT Filed: Sep. 30, 2020

(86) PCT No.: PCT/EP2020/077403
§ 371 (c)(1),
(2) Date: Apr. 1, 2022

(87) PCT Pub. No.: WO2021/064042
PCT Pub. Date: Apr. 8, 2021

(65) Prior Publication Data
US 2023/0270211 A1 Aug. 31, 2023

(30) Foreign Application Priority Data
Oct. 2, 2019 (DE) .......................... 102019126598.3

(51) Int. Cl.
*A43D 1/02* (2006.01)
*A43D 8/02* (2006.01)
(52) U.S. Cl.
CPC ............... *A43D 1/025* (2013.01); *A43D 8/02* (2013.01)

(58) Field of Classification Search
CPC ...... A43D 1/025; A43D 1/02; A43D 2200/60; A43D 3/02; A43D 119/00; A43D 1/022;
(Continued)

(56) References Cited

U.S. PATENT DOCUMENTS 6,205,230 B1 * 3/2001 Sundman ............... G01B 21/20
382/100
7,206,718 B2 * 4/2007 Cavanagh ............ A61B 5/6829
702/155

(Continued)

FOREIGN PATENT DOCUMENTS

DE 4404695 A1 8/1995

*Primary Examiner* — Michael P Stafira
(74) *Attorney, Agent, or Firm* — Jonathan M. D'Silva; MMI Intellectual Property (57) ABSTRACT

An optical foot sole scanning apparatus, comprising: a) an element that is substantially in the shape of a plate or a wedge in the unloaded state and is made of a resilient material, having a foot placement side facing a foot sole of a human foot to be scanned when in use and having a scanner side, wherein the resilient material is at least partially light-transmissive, b) an optical scanner that is arranged on the scanner side of the element and is configured to emit electromagnetic radiation through the element at least in part onto the foot placement side of the element when in use and to record data when in use, and c) an evaluation unit that is connected to the optical scanner and is set up to perform a reconstruction of the three-dimensional shape of the foot sole from the data recorded by the optical scanner, and an orthopedic foot sole scanning system having same, an insole production apparatus having same, a method for ascertaining a three-dimensional shape of an insole having same, and a method for automatically producing an insole having same.

13 Claims, 8 Drawing Sheets (58) Field of Classification Search
CPC ...... A43D 1/027; A43D 1/08; A43D 2200/10; A43D 25/183; A43D 999/00; A43D 1/04; A43D 95/10; A43D 11/14; A43D 3/145; A43D 3/1458; A43D 111/00; A43D 39/00; A43D 8/00; A43D 25/06; A43D 25/18; A43D 25/20; A43D 117/00; A43D 8/02; A43D 111/006; A43D 1/06; A43D 111/003; A43D 8/10; A43D 11/003; A43D 3/00; A43D 8/32; A43D 1/00; A43D 2200/00; A43D 25/07; A43D 3/027; A43D 3/08; A43D 3/1433; A43D 11/12; A43D 25/047; A43D 3/1408; A43D 11/01; A43D 11/145; A43D 2200/20; A43D 2200/40; A43D 25/08; A43D 3/021; A43D 37/00; A43D 8/34; A43D 9/00; A43D 95/08; A43D 95/14; A43D 2200/30; A43D 3/022; A43D 8/12; A43D 8/16; A43D 8/26; A43D 86/00; A43D 95/00; A43D 95/28; A43D 25/00; A43D 29/00; A43D 3/14; A43D 44/00; A43D 5/00; A43D 8/04; A43D 8/36; A43D 8/38; A43D 87/00; A43D 95/02; G01B 11/24; G01B 11/25; G01B 11/2518; G01B 11/245; G01B 11/2504; G01B 11/022; G01B 11/03; G01B 11/22; G01B 21/00; G01B 11/00; G01B 11/02; G01B 11/2433; G01B 11/2513; G01B 11/002; G01B 11/2545; G01B 21/20; G01B 2290/20; G01B 2290/35; G01B 2290/40; G01B 2290/65; G01B 2290/70; G01B 5/0004; G01B 9/02003; G01B 9/02007; G01B 9/0201; G01B 9/0205; G01B 9/02091; G01B 11/024; G01B 11/06; G01B 11/26; G01B 11/28; G01B 21/18; G01B 5/0002; G01B 9/02; G01B 11/04; G01B 11/043; G01B 11/046; G01B 11/303; G01B 17/00; G01B 5/02; G01B 5/20; G01B 7/34

See application file for complete search history.

(56) References Cited

U.S. PATENT DOCUMENTS

| | | | |
|---|---|---|---|
| 10,452,054 B2* | 10/2019 | McInnis | A43B 7/141 |
| 2006/0070260 A1 | 4/2006 | Cavanagh et al. | |
| 2009/0247909 A1 | 10/2009 | Mukumoto | |
| 2014/0104395 A1* | 4/2014 | Rohaly | G01B 11/245 348/47 |
| 2016/0288440 A1* | 10/2016 | Louko | B29D 35/128 |
| 2017/0255185 A1* | 9/2017 | Hinshaw | A43D 1/025 |
| 2019/0082794 A1* | 3/2019 | Liu | G01B 5/20 |

* cited by examiner

Figure 1

(Prior art)

OPTICAL FOOT SOLE SCANNING APPARATUS AND INSOLE PRODUCTION APPARATUS HAVING SAME, METHOD FOR ASCERTAINING A THREE-DIMENSIONAL SHAPE OF AN INSOLE AND METHOD FOR AUTOMATICALLY PRODUCING AN INSOLE

The present invention relates to an optical foot sole scanning apparatus and an insole production apparatus having same, to a method for ascertaining a three-dimensional shape of an insole, and to a method for automatically producing an insole. The invention in particular relates to an orthopedic foot sole scanning system comprising an optical foot sole scanning apparatus.

Insoles serve a variety of purposes, including the alleviation of physical ailments such as arthritis, sciatica, overstrained feet, damaged pelvis or pelvic misalignment, or scoliosis due to leg length discrepancy. In addition, insoles are also used by symptom-free people for non-orthopedic purposes, such as to improve sports performances or levels of comfort when wearing shoes. Both standardized insoles and individualized insoles, that is to say insoles that have been adapted to the foot, are known. Individually manufactured insoles are better suited for alleviating said physical ailments and offer more comfort when they are worn.

Three standard methods for adapting the insoles to the patient are known: plaster models, foam impressions, and scanning methods. Conventionally, insoles are made from plaster impressions of the foot of the patient. To this end, plaster strips are wrapped around the foot to capture its shape and are then left to dry and harden. After the model has hardened, it is carefully removed from the foot of the patient and shipped to an orthopedics laboratory, which uses the negative to produce an insole. Due to the relatively large complexity of this method, it is only rarely used nowadays.

Alternatively, foot impressions can be created by pressing a foot into a box filled with foot-impression foam. The foot-impression foam is compressed or disintegrates at the locations where the foot is placed. The three-dimensional foam impression of the foot can be filled or scanned. However, using this method it is possible only with difficulty to test the influence of a correction on the foot position by means of an insole used for the purpose of the test and to image the corrected foot position.

In known scanning methods, the foot is placed on a glass plate of a scanning apparatus. The foot sole is scanned through the glass plate, similar to a flatbed scanner. Fundamentally, feet seek to make contact with the ground and, when placed on the glass plate, drop in the locations where they do not touch the glass plate. At the locations where the foot is in contact with the glass plate, the scanning apparatus scans the foot sole that is pressed flat against the glass plate. Due to these two effects, the foot shape in scanning apparatuses that have been used previously is flattened relative to the natural foot shape. The data obtained are modeled manually by an orthopedic technician to simulate a natural foot shape. The modeling depends on the experience of the orthopedic technician and is frequently based on estimations regarding the natural foot shape, resulting in great variations in the quality of the imaging and thus of the insole. Imaging a corrected foot position is likewise possible only with difficulty when using the scanning method.

For insoles for non-orthopedic purposes, enhanced wear comfort and prevention of the development of misalignments due to physiological foot loading are an essential criterion. Any foot loading that is not optimum causes a decrease in wear comfort. Feet are loaded optimally when they walk on soft ground, such as forest soil. The foot sole scanning apparatuses known from the prior art are also unable to create an imprint of a foot sole under natural, optimum loading.

It is therefore the object of the present invention to provide a foot sole scanning apparatus that allows the easy scanning and more accurate imaging of foot soles with and without correction of the foot position under optimum loading.

DESCRIPTION OF THE INVENTION

According to the invention, this object is achieved by an optical foot sole scanning apparatus, comprising: a) an element that is substantially in the shape of a plate or a wedge in the unloaded state and is made of a resilient material, having a foot placement side facing a foot sole of a human foot to be scanned when in use and having a scanner side, wherein the resilient material is at least partially light-transmissive, b) an optical scanner that is arranged on the scanner side of the element and is configured to emit electromagnetic radiation through the element at least in part onto the foot placement side of the element when in use and to record data when in use, and c) an evaluation unit that is connected to the scanner and is set up to perform a reconstruction of the three-dimensional shape of the foot sole from the data recorded by the scanner.

The invention furthermore provides an orthopedic foot sole scanning system, comprising: an optical foot sole scanning apparatus as claimed in one of claims 1 to 9, and at least one silicone pillow that is suitable for changing a position of at least one foot placed on the element by being introduced under at least one arch.

The invention furthermore provides an insole production apparatus, comprising an optical foot sole scanning apparatus as claimed in one of claims 1 to 9, and an insole fabrication device that is in data-connection with the optical foot sole scanning apparatus.

The invention additionally provides a method for ascertaining a three-dimensional shape of an insole, comprising the steps of: providing an optical foot sole scanning apparatus as claimed in one of claims 1 to 9, placing at least one foot with the foot sole on the element, scanning the foot sole(s) with the optical scanner, transferring the data ascertained by the scanning from the scanner to the evaluation unit, reconstructing the three-dimensional shape of the foot sole, and calculating a three-dimensional shape of at least one insole for improving the weight distribution on the foot in the loaded state from the reconstructed shape of the foot sole by means of the evaluation unit. In particular, the step of changing a position of the at least one foot by introducing at least one silicone pillow under an arch of the at least one foot for correcting a misalignment can be provided here, wherein the step of calculating preferably comprises calculating a three-dimensional shape of at least one insole for improving the weight distribution on the foot in the loaded state including correcting a misalignment from the reconstructed shape of the foot sole by means of the evaluation unit.

The invention additionally provides a method for automatically producing an insole, comprising the steps of: providing an insole production apparatus as claimed in claim 11 or 12, placing at least one foot with the foot sole on the element, scanning the foot sole(s) with the optical scanner, transferring the data ascertained by the scanning from the optical scanner to the evaluation unit, reconstructing the three-dimensional shape of the foot sole, and calculating a three-dimensional shape of at least one insole for improving the weight distribution on the foot in the loaded state from the reconstructed shape of the foot sole by means of the evaluation unit, and fabricating the insole by means of the insole fabrication device. The insole production apparatus preferably comprises here an orthopedic foot sole scanning system as claimed in one of claims 1 to 9 and an insole fabrication device that is in data-connection with the optical foot sole scanning apparatus. Alternatively or additionally, provision may be made that the method comprises the step of changing a position of the at least one foot by introducing at least one silicone pillow under an arch of the at least one foot for correcting a misalignment. The calculating then advantageously comprises calculating a three-dimensional shape of at least one insole for improving the weight distribution on the foot in the loaded state including correcting a misalignment from the reconstructed shape of the foot sole by means of the evaluation unit.

Provision is advantageously made in the optical foot sole scanning apparatus for the resilient material to comprise silicone gel.

In a particular embodiment of the invention, provision may be made that the Shore OO hardness of the resilient material lies below 50.

Provision may expediently be made that the element has on the foot placement side a polyurethane protective coating that is preferably disinfectable.

The disinfectable polyurethane protective coating preferably has a layer thickness of between 2 μm and 100 μm.

Alternatively or additionally, the scanner comprises a 2D or 3D laser scanner.

In a further particular embodiment, the optical scanner additionally captures the intensity of the reflected signal.

The element preferably has a layer thickness of between 1 cm and 10 cm.

The optical scanner expediently has a capturing accuracy of 1 mm or better.

Provision is made in particular in the case of the insole production apparatus for the insole fabrication device to comprise a milling cutter and/or a 3D printer.

In a further particular embodiment of the invention, provision may be made that the method for ascertaining a three-dimensional shape of an insole further comprises the step of: changing a position of the at least one foot by introducing at least one silicone pillow under an arch of the at least one foot for correcting a misalignment before scanning takes place.

The method for ascertaining a three-dimensional shape of an insole can furthermore make provision for calculating a three-dimensional shape of the insole by means of the evaluation unit to comprise automatically performing the steps of: cutting out the foot shape, selecting an insole size based on the scanned foot sole or the reconstructed shape of the foot sole, and selecting the material thickness of the insole based on the reconstructed shape of the foot sole.

Finally, the method for automatically producing an insole can make provision for calculating a three-dimensional shape of the insole from the ascertained data by means of the evaluation unit to comprise automatically performing the steps of: cutting out the foot shape, selecting an insole size based on the scanned foot sole or the reconstructed shape of the foot sole, and selecting the material thickness of the insole based on the reconstructed shape of the foot sole.

The invention is based on the surprising insight that a naturally loaded foot shape can be imaged by means of an optical scanner by using a resilient element that is in the shape of a plate in the unloaded state, wherein the naturally loaded foot shape can serve as a template for an insole without any manual reworking.

Further features and advantages of the invention are evident from the attached claims and the description below, in which an exemplary embodiment of the present invention is described with reference to the schematic drawings. In the figures:

Figure 1:
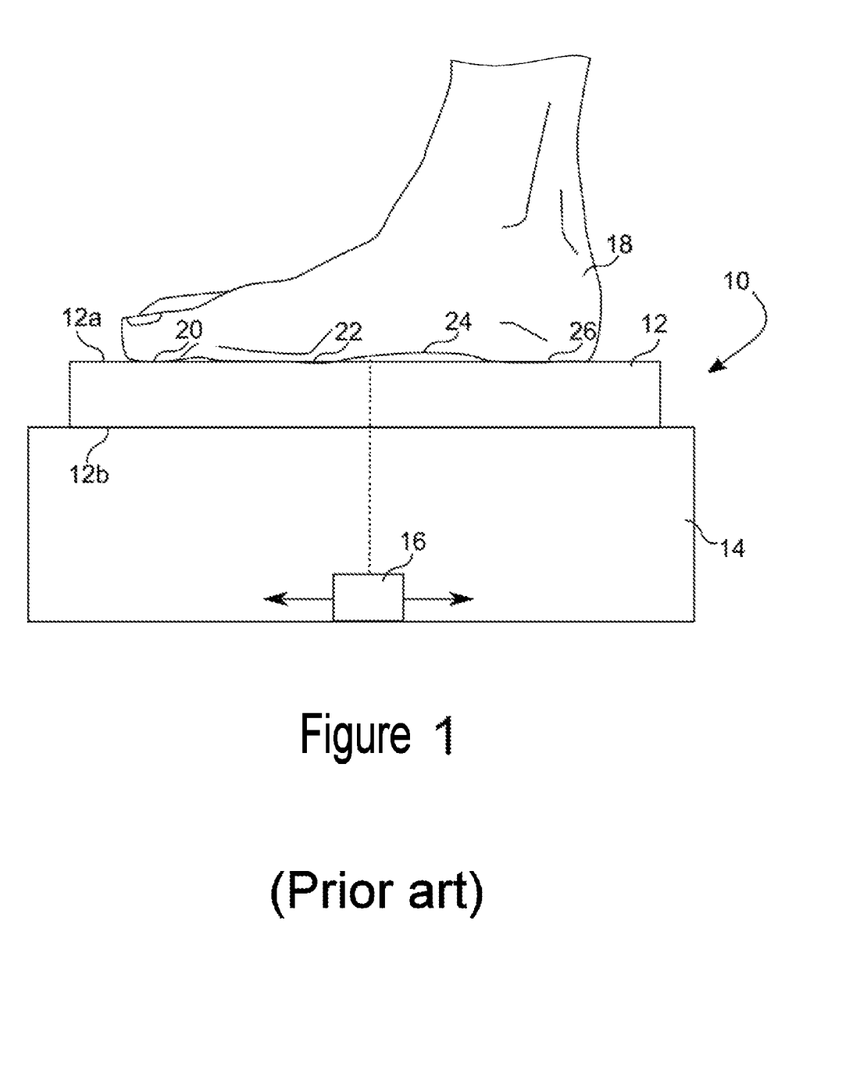
FIG. 1 shows a sectional view of an optical foot sole scanning apparatus according to the prior art in use with a view of the longitudinal arch of a foot to be scanned.

FIG. 1 shows a sectional view of an optical foot sole scanning apparatus 10 according to the prior art in use with a view of the longitudinal arch of a foot 18 to be scanned. The optical foot sole scanning apparatus 10 comprises a glass plate 12 with a foot placement side 12*a* and a scanner side 12*b*, wherein a scanner 14 having a scanner unit 16 is arranged on the scanner side 12*b* of the glass plate 12. A foot 18 is placed on the foot placement side 12*a* of the glass plate 12 during operation. The different regions of the foot 18, the toe region 20, the ball of the foot 22, the arch 24, and the heel 26 are imaged by the scanner 14 during operation. The shape of the foot 18 changes owing to the placement of the foot 18 on the hard glass plate 12. The toe region 20, the ball of the foot 22, and the heel 26 are placed flat against the glass plate 12 over wide areas. Even the arch 24 has dropped relative to the unloaded and/or to the naturally loaded foot shape.

Figure 2:
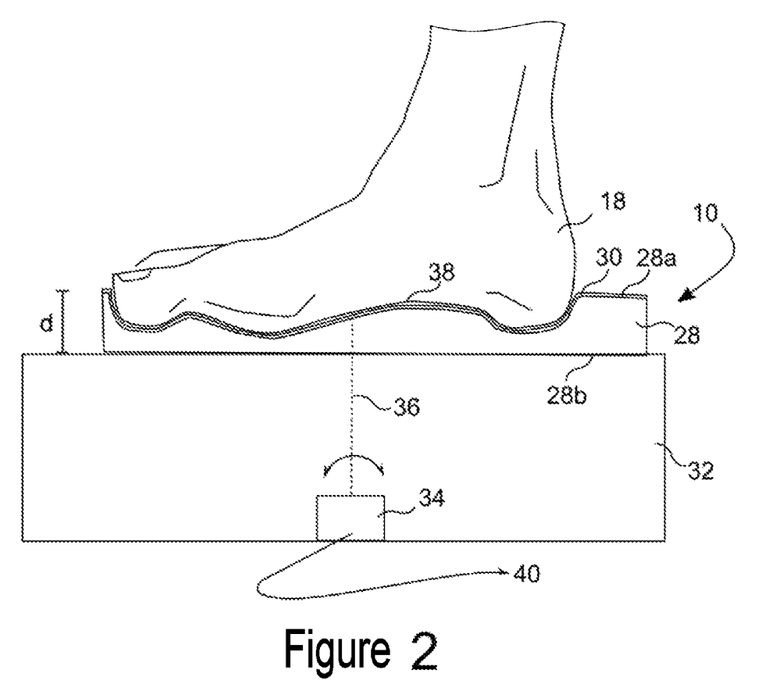
FIG. 2 shows a sectional view of an optical foot sole scanning apparatus according to a particular embodiment of the invention in use with a view of the longitudinal arch of a foot to be scanned.

FIG. 2 shows a sectional view of an optical foot sole scanning apparatus 10 according to a particular embodiment of the invention in use with a view of the longitudinal arch of a foot 18 to be scanned. The optical foot sole scanning apparatus 10 comprises an element 28 that is in the shape of a plate in the unloaded state and is made from a resilient material. The element 28 has a foot placement side 28a, a scanner side 28b, and a layer thickness d. The layer thickness d of the element 28 is preferably between 1 cm and 10 cm, with particular preference between 1.5 cm and 5 cm. The layer thickness d of the element 28 is here preferably adapted to the weight of the person whose foot soles are intended to be scanned. For people of greater weight, foot sole scanning apparatuses 10 having an element 28 with a greater layer thickness d are preferably used. To this end, the element 28 may also be interchangeable. The resilient material from which the element 28 is composed is at least partially light-transmissive silicone gel. The Shore OO hardness of the resilient material is preferably below 50, with particular preference below 15. Provision may in particular be made that the Shore OO hardness of the resilient material lies below 5. All Shore OO hardnesses specified here correspond to values measured in accordance with the ASTM D2240 standard.

A disinfectable polyurethane protective coating 30 is applied on the foot placement side 28a of the element 28. The layer thickness of the disinfectable polyurethane protective coating 30 is preferably between 2 µm and 100 µm, with particular preference between 10 µm and 50 µm, and with the greatest preference is 25 µm. The disinfectable polyurethane protective coating 30 makes it possible, among other things, to clean and/or disinfect the element 28 particularly easily. An optical scanner 32 is arranged on the scanner side 28b of the element 28. The optical scanner 32 comprises a 3D laser scanner 34. The 3D laser scanner is used to scan a three-dimensional shape of the foot placement side 28a of the element 28 during operation and to perform, based on the data thus obtained, a reconstruction of the three-dimensional shape of the plantar aspect of a foot 18 placed thereon. According to the invention it is also possible to place two feet 18 on the element 28 at the same time and to perform a reconstruction of the three-dimensional shape of the plantar aspects of both feet 18.

For reconstructing the plantar aspect(s) of one or two feet 18, a laser beam 36 is scanned over the entire foot placement side 28a of the element 28. The resilient material of the element 28 is selected with respect to its hardness such that the foot placement side of the element 28 adapts to the shape of the foot sole 38, and therefore a scan of the foot placement side of the element 28 comprises a complete scan of the foot sole 38. The terms "foot sole" and "plantar aspect of the foot" are used synonymously in this application. The optical foot sole scanning apparatus 10 additionally comprises an evaluation unit 40 (not explicitly illustrated here, cf. FIG. 5), which is connected to the optical scanner 32. The evaluation unit 40 is set up to calculate from the data recorded by the optical scanner 32 a reconstruction of the three-dimensional shape of the plantar aspect of the foot 18 or the feet 18 that can be used as a template for an insole or correspond to it. During the reconstruction, provision may be made that the foot 18 or the feet 18 is or are cut, preferably automatically, out of the scanned foot placement side 28a. Provision may furthermore be made that the further processing comprises selecting an insole size that corresponds to a size of the foot 18 or the feet 18 from a selection of standard sizes for insoles. Provision may further be made for the calculation of the three-dimensional shape of the insole to comprise selecting a material thickness of the insole. Provision can in particular be made that for a person with a higher arch whose feet 18 are scanned, a thicker material thickness of the insole is selected than for a person with a lower arch whose feet are scanned.

Figure 3:
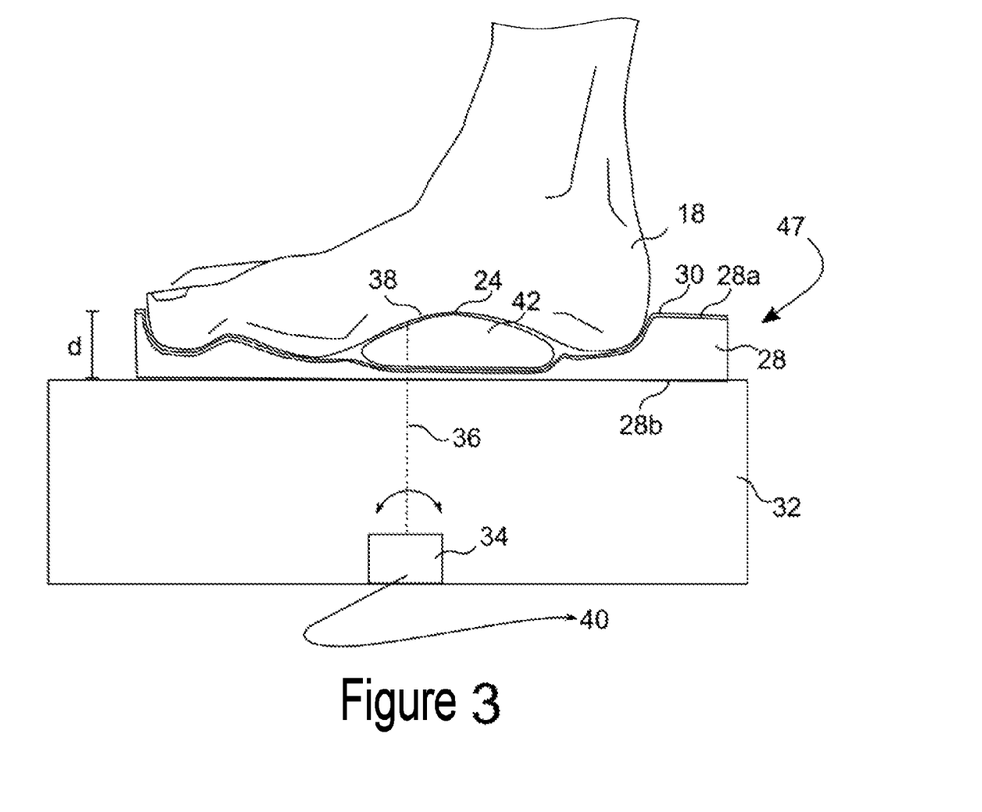
FIG. 3 shows a sectional view of an orthopedic foot sole scanning system according to a further particular embodiment of the invention in use with a view of the longitudinal arch, determining the shape of the foot sole, of a foot to be scanned.

FIG. 3 shows a sectional view of an orthopedic foot sole scanning system 47 according to a further particular embodiment of the invention in use with a view of the longitudinal arch of a foot 18 to be scanned. The orthopedic foot sole scanning system 47 comprises all the features of the invention shown in FIG. 2. Furthermore, a silicone pillow 42 is arranged here on or under the disinfectable polyurethane protective coating 30 of the element 28 below the foot sole 38 at the arch 24. The arch significantly determines the position of the foot 18 and the three-dimensional shape of the foot sole. The position of the foot 18, and thus the three-dimensional shape of the foot sole 38, is orthopedically corrected by the arrangement of the silicone pillow under the foot sole. The silicone pillow 42 preferably consists of the same light-transmissive material as the element 28. In this way, the laser beam 36 emitted by the 3D laser scanner 34 is not diffracted, or diffracted only slightly, at the interfaces between the silicone pillow 42 and the element 28, or the disinfectable polyurethane protective coating 30. A reconstruction of a three-dimensional shape of the plantar aspect of a foot 18 placed on the element 28 can thus also be performed during an orthopedic correction performed with the silicone pillow 42. The silicone pillows 42 effect a correction that can correspond to the correction of insoles that are to be created. Preferably, silicone pillows 42 of varying sizes are placed under the foot 18 or under the element 28 in succession to optimize the orthopedic correction of the foot 18. Once each of the silicone pillows 42 has been placed, in each case similar to the manner described in connection with FIG. 2, reconstructions of the three-dimensional shape of the foot sole 38 are performed with varying loading. On the basis of the results of the scans thus achieved, an orthopedic technician can easily check for which shape of the silicone pillows 42 an orthopedic correction of a scanned foot 18 is performed optimally, that is to say which shape of the foot sole 38 that was scanned under loading best matches the shape of a healthy foot sole 38. The shape of the insole to be created can then be selected according to the shape of the silicone pillows taking into account the foot position.

Figure 4:
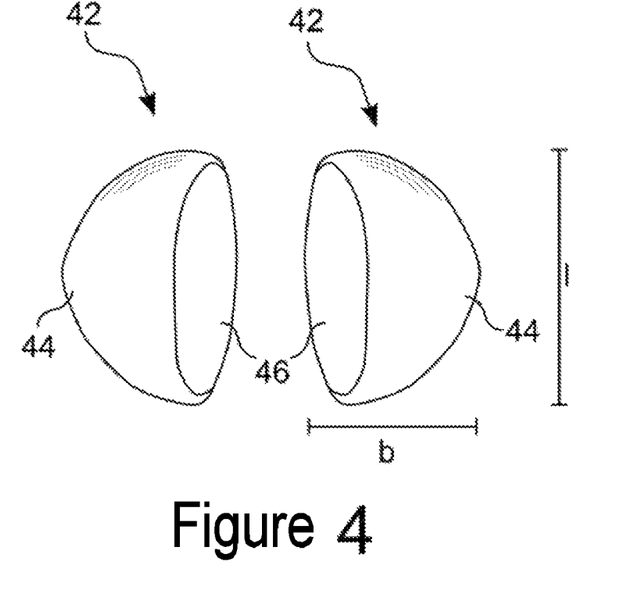
FIG. 4 shows an individual view of a pair of the silicone pillows used in FIG. 3 for changing the foot position.

FIG. 4 shows an individual view of a pair of the silicone pillows 42 used in FIG. 3, of which each is set up to be placed on the plantar aspect of the foot 18 in each case under an arch 24 and to change thereby the foot position. The silicone pillows 42 have a flatly tapering region 44 and a raised region 46. The flatly tapering region 44 is set up to be placed at the height of the arch 24 in a region of the foot 18 facing away from the body's core defined by the sagittal plane. The raised region 46 is set up to be placed at the height of the arch 24 in a region of the foot 18 facing the body's core defined by the sagittal plane and has a height of between 1 cm and 6 cm, for example. The silicone pillows 42 are available with different lengths l and widths b and are adapted to feet of different sizes. The length l can here be between 5 cm and 20 cm, for example. The width b can be between 3 cm and 8 cm, for example. Larger or smaller embodiments of the silicone pillows 42 are likewise conceivable.

Figure 5:
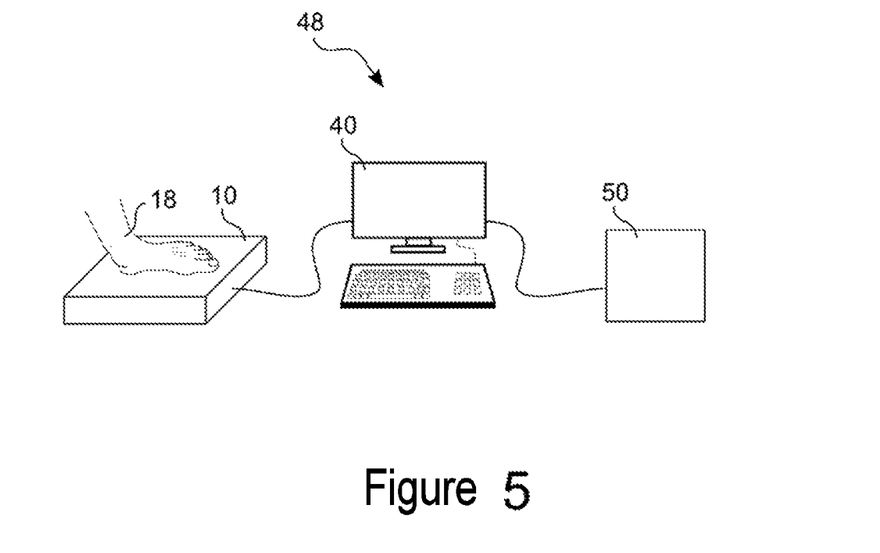
FIG. 5 shows a schematic illustration of an insole production apparatus according to a particular embodiment of the invention.

FIG. 5 shows a schematic illustration of an insole production apparatus 48 according to a particular embodiment of the invention. The insole production apparatus 48 comprises an optical foot sole scanning apparatus 10 according to the embodiment of the invention shown in FIG. 2 and an insole fabrication device 50. The insole fabrication device 50 can for example be a milling cutter that is suitable for fabricating insoles or a 3D printer suitable for fabricating insoles. The insole production apparatus 48 serves for automatically fabricating insoles. To this end, a foot 18, or a plurality of feet 18, is placed with its plantar aspect on the foot sole scanning apparatus 10, and a three-dimensional reconstruction of the plantar aspect of the foot 18, or the feet 18, is performed according to the embodiment of the invention described in connection with FIG. 2. The reconstruction is transmitted to the insole fabrication device 50, which, preferably automatically, fabricates insoles according to the reconstruction. For fabrication purposes, the insole can be milled using a milling cutter (not explicitly illustrated) from a blank or be printed using a suitable 3D printer (likewise not explicitly illustrated).

Figure 6A:
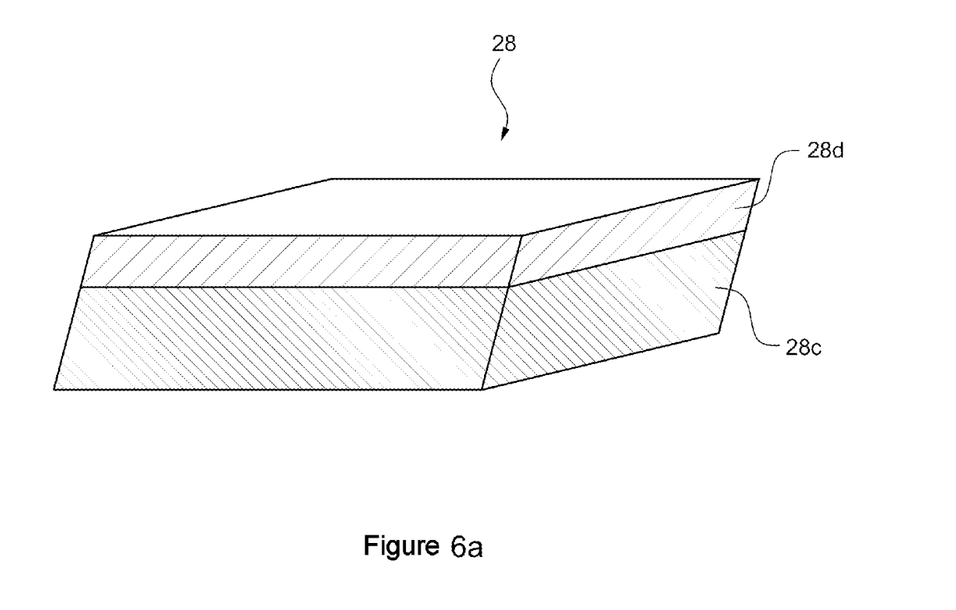
FIG. 6*a* shows a perspective view of an element that is in the shape of a plate in the unloaded state according to a further particular embodiment of the present invention.

The element 28 made of resilient material shown in FIG. 6a in this example consists of two layers 28c and 28d, which are made from silicone gels having different Shore hardnesses OOO and are arranged one on top of the other. The element 28 could of course also consist of more than two layers having different Shore hardnesses.

A disinfectable polyurethane protective coating (not shown) is advantageously located on the upper one 28d of the two layers 28c and 28d.

Figure 7A:
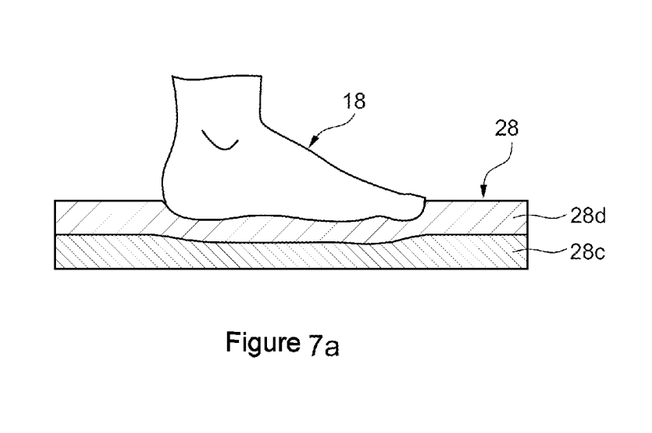
FIG. 7*a* shows a side view of the element of FIG. 6*a* in the loaded state during use.

The two layers 28c and 28d can have different thicknesses. Alternatively or additionally, the upper layer 28d can be softer than the lower layer 28c so as to be able to scan a foot 18 that is placed thereon (see FIG. 7a) over a particularly large area and in the form of a shell. This is particularly advantageous due to an increased or maximum pressure distribution in the case of diabetic foot syndrome and rheumatic feet.

Figure 6B:
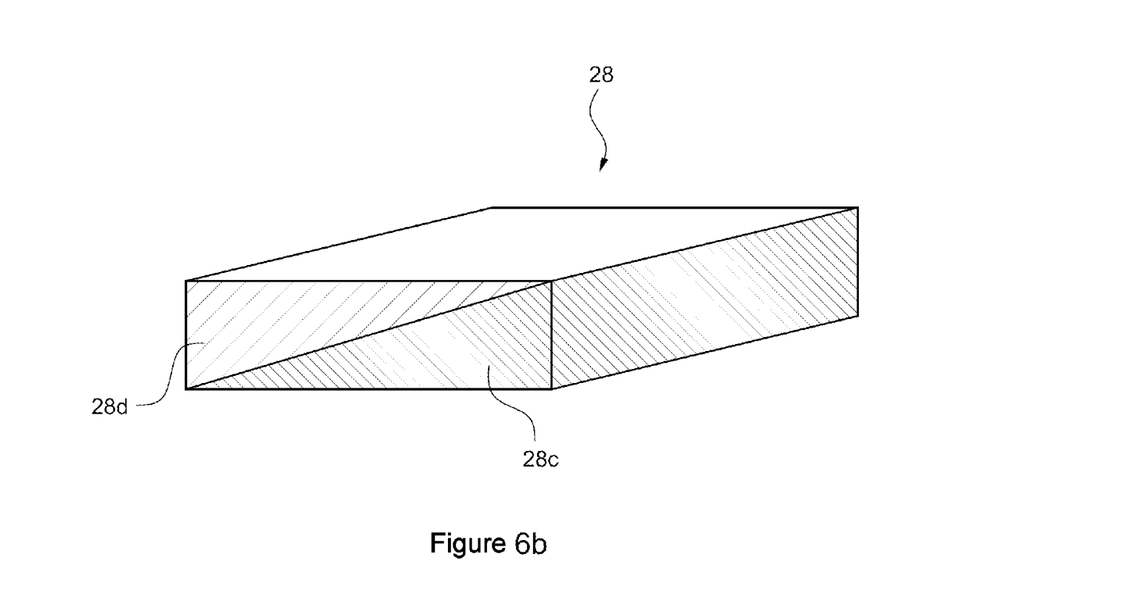
FIG. 6*b* shows a perspective view of an element that is in the shape of a plate in the unloaded state according to a further particular embodiment of the present invention.

The element 28 shown in FIG. 6b differs from the element shown in FIG. 6a substantially in that the two layers 28c and 28d do not have a constant thickness but are wedge-shaped and arranged such that, once placed one on top of the other, they form an assembled element having a constant thickness.

Figure 7B:
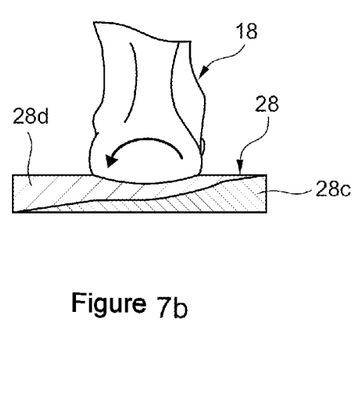
FIG. 7*b* shows a side view of the element of FIG. 6*b* in the loaded state during use.

Owing to the non-uniform layer thickness or the wedge-shaped design, a foot to be scanned can be tilted inwardly or outwardly (pronation/supination) in the sense of a position correction (see also FIG. 7b). It is thus possible to attain a desired position correction before a scan is performed. However, this is only an example.

Figure 6C:
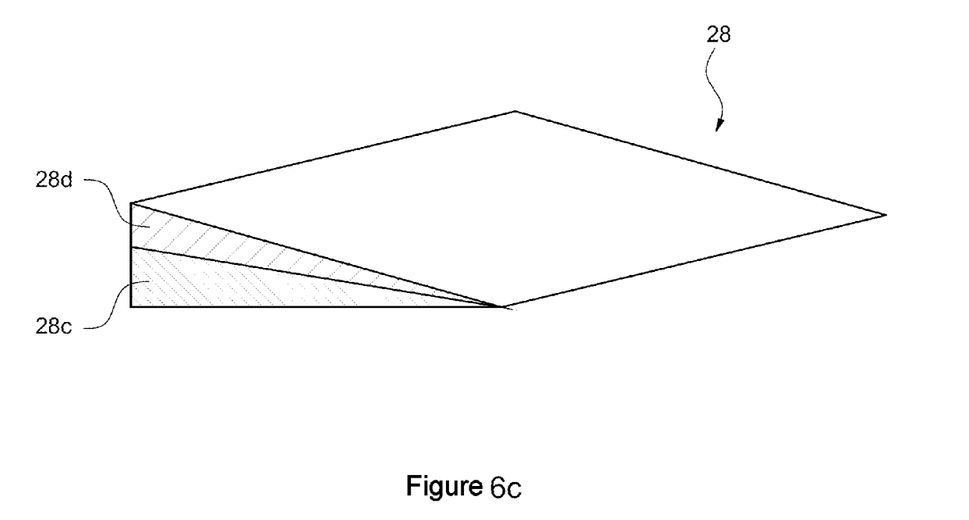
FIG. 6*c* shows a perspective view of an element that is in the shape of a wedge in the unloaded state according to a further particular embodiment of the present invention.
Figure 7C:
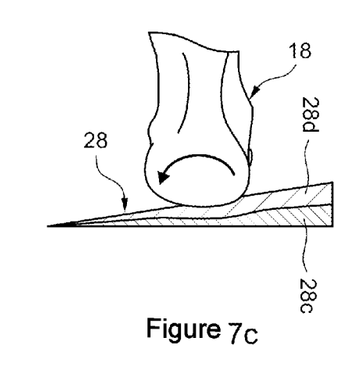
FIG. 7*c* shows a side view of the element of FIG. 6*c* in the loaded state during use.

The element 28 shown in FIG. 6c differs from the element shown in FIG. 7b in that the two layers 28c and 28d are arranged one on top of the other in a manner such that the resulting element 28 is wedge-shaped in cross section. The resulting inclined surface (foot placement side 28a) makes a position correction of a foot (see also FIG. 7c) possible.

Figure 6D:
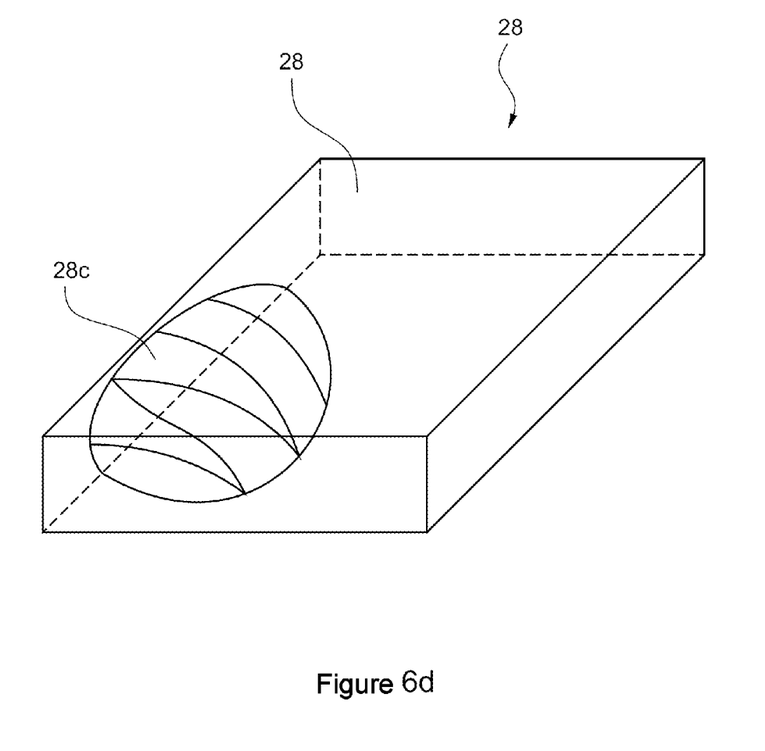
FIG. 6*d* shows a perspective view of an element that is substantially in the shape of a plate in the unloaded state according to a further particular embodiment of the present invention.
Figure 7D:
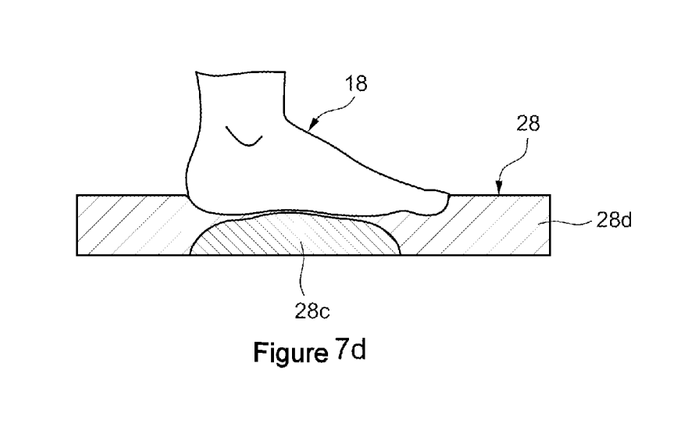
FIG. 7*d* shows a side view of the element of FIG. 6*d* in the loaded state during use.
Figure 7E:
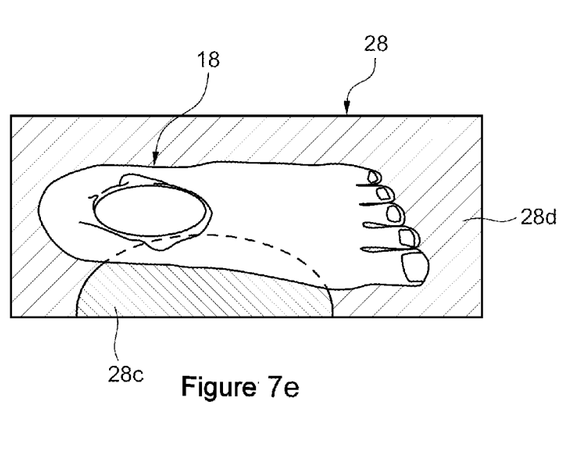
FIG. 7*e* shows a plan view from above of the element of FIG. 6*d* in the loaded state during use.

The element 28 shown in FIG. 6d differs from the element shown in FIG. 6a in that it does not consist of two layers that were placed one on top of the other but that inside a layer 28d, a region 28e made of silicone gel having—in this example only—a Shore hardness that differs from the Shore hardness of the layer 28d is located. The region 28e or the resulting element 28 can be used for a position correction of a foot for example by erecting the arch before a scan is performed (see also FIGS. 7d and 7e).

In the examples shown in FIGS. 6 and 7, the lower layer 2c has a Shore hardness of for example 32 (measured using a Bareiss durometer OOO) and the upper layer 28d has a Shore hardness of 32 (measured using the Bareiss durometer OOO). Generally speaking, the plate-shaped or wedge-shaped element or at least one layer of the plate-shaped element, wherein the latter may also have more than two layers, can have one of the previously mentioned Shore hardness values. In even more general terms, the plate-shaped or wedge-shaped element or a layer of a multilayer plate-shaped or wedge-shaped element can have a Shore hardness in the range from 20 to 40 Shore OOO (measured using the Bareiss durometer OOO).

Alternatively or additionally, the plate-shaped or wedge-shaped element can have a time-independent residual pressure deformation in the range from 1% to 4%, preferably of 2%. The value mentioned previously can relate for example to a layer thickness of the element of 20.5±0.1 mm in the unloaded state.

If the plate-shaped or wedge-shaped element consists of only one layer, it can be produced, for example, as follows: If it consists, for example, of a two-component silicone crosslinked at room temperature, the components are mixed directly before a mold is filled. Next, the silicone is hardened in the mold without further pressure or heat.

If a disinfectable polyurethane protective coating is also intended to be applied, the latter is already located in the mold beforehand and bonds with the use of a primer during the hardening process.

If the plate-shaped or wedge-shaped element consists of more than one layer, for example the second layer can be produced by the size of the mold being increased for the second layer and the mold then being filled again with a, preferably harder, lower silicone.

The features of the invention which are disclosed in the description above, in the drawings, and in the claims may be essential, both individually and in any desired combinations, for the implementation of the invention in its various embodiments.

LIST OF REFERENCE SIGNS

10 Optical foot sole scanning apparatus
12 Glass plate
12a Foot placement side
12b Scanner side
14 Scanner
16 Scanner unit
18 Foot
20 Toe region
22 Ball of the foot
24 Arch
26 Heel
28 Element
28a Foot placement side
28b Scanner side
28c, 28d Layers
28e Region
30 Disinfectable polyurethane protective coating
32 Optical scanner
34 3D laser scanner
36 Laser beam
38 Foot sole
40 Evaluation unit
42 Silicone pillow
44 Flatly tapering region
46 Raised region
47 Orthopedic foot sole scanning system
48 Insole production apparatus
50 Insole fabrication device
d Thickness of the element in the unloaded state
l Length of the silicone pillow
b Width of the silicone pillow

The invention claimed is:

1. An orthopedic foot sole scanning system, comprising:
an optical foot sole scanning apparatus comprising:
   a) an element that is substantially in the shape of a plate or a wedge in the unloaded state and is made of a resilient material, having a foot placement side facing a foot sole of a human foot to be scanned when in use and having a scanner side, wherein said resilient material is at least partially light-transmissive;
   b) an optical scanner that is arranged on said scanner side of said element and is configured to emit electromagnetic radiation through said element at least in part onto said foot placement side of said element when in use and to record data when in use; and
   c) an evaluation unit that is connected to said optical scanner and is set up to perform a reconstruction of the three-dimensional shape of the foot sole from said data recorded by said optical scanner; and
at least one silicone pillow that is suitable for changing a position of at least one foot placed on said element by being introduced under at least one arch.

2. A method for ascertaining a three-dimensional shape of an insole, comprising the steps of:
providing an optical foot sole scanning apparatus comprising:
   a) an element that is substantially in the shape of a plate or a wedge in the unloaded state and is made of a resilient material, having a foot placement side facing a foot sole of a human foot to be scanned when in use and having a scanner side, wherein the resilient material is at least partially light-transmissive;
   b) an optical scanner that is arranged on the scanner side of the element and is configured to emit electromagnetic radiation through the element at least in part onto the foot placement side of the element when in use and to record data when in use; and
   c) an evaluation unit that is connected to the optical scanner and is set up to perform a reconstruction of the three-dimensional shape of the foot sole from the data recorded by the optical scanner;
placing at least one foot with the foot sole on the element;
changing a position of the at least one foot by introducing at least one silicone pillow under an arch of the at least one foot for correcting a misalignment before scanning takes place;
scanning the foot sole(s) with the optical scanner;
transferring the data ascertained by the scanning from the optical scanner to the evaluation unit;
reconstructing the three-dimensional shape of the foot sole; and
calculating a three-dimensional shape of at least one insole for improving the weight distribution on the foot in the loaded state from the reconstructed shape of the foot sole by means of the evaluation unit.

3. The method for ascertaining a three-dimensional shape of an insole of claim 2, wherein calculating a three-dimensional shape of the insole by means of the evaluation unit comprises automatically performing the steps of:
cutting out the foot shape;
selecting an insole size on the basis of the scanned foot sole or the reconstructed shape of the foot sole; and
selecting the material thickness of the insole on the basis of the reconstructed shape of the foot sole.

4. A method for automatically producing an insole, comprising the steps of:
providing an insole production apparatus comprising:
   an optical foot sole scanning apparatus that further comprises:
      a) an element that is substantially in the shape of a plate or a wedge in the unloaded state and is made of a resilient material, having a foot placement side facing a foot sole of a human foot to be scanned when in use and having a scanner side, wherein the resilient material is at least partially light-transmissive;
      b) an optical scanner that is arranged on the scanner side of the element and is configured to emit electromagnetic radiation through the element at least in part onto the foot placement side of the element when in use and to record data when in use; and
      c) an evaluation unit that is connected to the optical scanner and is set up to perform a reconstruction of the three-dimensional shape of the foot sole from the data recorded by the optical scanner; and
   an insole fabrication device that is in data connection with the optical foot sole scanning apparatus;
placing at least one foot with the foot sole on the element;
scanning the foot sole(s) with the optical scanner;
transferring the data ascertained by the scanning from the optical scanner to the evaluation unit;
reconstructing the three-dimensional shape of the foot sole; and
calculating a three-dimensional shape of at least one insole for improving the weight distribution on the foot in the loaded state from the reconstructed shape of the foot sole by means of the evaluation unit wherein calculating a three-dimensional shape of the insole from the ascertained data by means of the evaluation unit comprises automatically performing the steps of:
cutting out the foot shape;
selecting an insole size on the basis of the scanned foot sole or the reconstructed shape of the foot sole; and
selecting the material thickness of the insole on the basis of the reconstructed shape of the foot sole; and
fabricating the insole by means of the insole fabrication device.

5. The orthopedic foot sole scanning system of claim 1, wherein said resilient material comprises silicone gel.

6. The orthopedic foot sole scanning system of claim 1, wherein the Shore OO hardness of said resilient material is under 50.

7. The orthopedic foot sole scanning system of claim 1, wherein said element has a polyurethane protective coating on said foot placement side.

8. The orthopedic foot sole scanning system of claim 1, wherein said polyurethane protective coating has a layer thickness of between 2 µm and 100 µm.

9. The orthopedic foot sole scanning system of claim 1, wherein said polyurethane protective coating is disinfectable.

10. The orthopedic foot sole scanning system of claim 1, wherein said optical scanner comprises a 2D or 3D laser scanner.

11. The orthopedic foot sole scanning system of claim 1, wherein said optical scanner additionally captures the intensity of the reflected signal.

12. The orthopedic foot sole scanning system of claim 1, wherein said element has a layer thickness of between 1 cm and 10 cm in the unloaded state.

13. The orthopedic foot sole scanning system of claim 1, wherein said optical scanner has a capturing accuracy of 1 mm or better.

\* \* \* \* \*